United States Patent
Gao et al.

(10) Patent No.: US 6,980,662 B1
(45) Date of Patent: Dec. 27, 2005

(54) DEVICE FOR PRESENTING ACOUSTICAL AND VIBRATORY STIMULI AND METHOD OF CALIBRATION

(75) Inventors: Shawn X. Gao, Cerritos, CA (US); Daniel J. Freed, Santa Monica, CA (US)

(73) Assignee: House Ear Institute, Los Angeles, CA (US)

( * ) Notice: Subject to any disclaimer, the term of this patent is extended or adjusted under 35 U.S.C. 154(b) by 496 days.

(21) Appl. No.: 09/972,407

(22) Filed: Oct. 5, 2001

Related U.S. Application Data

(60) Provisional application No. 60/238,749, filed on Oct. 6, 2000.

(51) Int. Cl.[7] ............................................. H04R 29/00
(52) U.S. Cl. ......................................... 381/59; 381/60
(58) Field of Search ........................... 381/56–60, 120; 73/585

(56) References Cited

U.S. PATENT DOCUMENTS

| | | |
|---|---|---|
| 4,109,107 A | 8/1978 | Boast |
| 4,586,194 A | 4/1986 | Kohashi et al. |
| 5,386,475 A * | 1/1995 | Birck et al. ................... 381/60 |

* cited by examiner

*Primary Examiner*—Ping Lee
(74) *Attorney, Agent, or Firm*—Blakely Sokoloff Taylor & Zafman LLP

(57) ABSTRACT

A hearing test device is capable of presenting a variety of acoustical or vibratory stimuli and can be easily calibrated. Transfer functions for the device are calculated at two different attenuation levels to derive the characteristic impedance and sensitivity of the acoustic or vibratory transducer. The predicted sound pressure level emitted by the transducer may then be calculated as a function of input signal and attenuation.

8 Claims, 3 Drawing Sheets

DEVICE FOR PRESENTING ACOUSTICAL AND VIBRATORY STIMULI AND METHOD OF CALIBRATION

BACKGROUND OF THE INVENTION

This application claims priority of provisional patent application Ser. No. 60/238,749 filed Oct. 6, 2000.

1. Field of the Invention

The present invention relates generally to the field of equipment for testing hearing. More particularly, the invention pertains to a hearing test device that is capable of presenting a variety of acoustical or vibratory stimuli and that can be easily calibrated.

2. Background

To perform a hearing test, it is necessary to present acoustical or vibratory stimuli at precisely controlled levels. Devices that perform this function, called audiometers, have been available for many years. Audiometers are optimized for presenting certain types of stimuli, such as pure tones and noise, which are used in traditional hearing tests. These stimuli are typically generated internally. All other stimuli must be provided by an outboard audio playback device, such as a tape player or CD player, which is supplied by the user and connected to the audiometer's external audio input.

Conventional audiometers are calibrated using a manual procedure. For each type of internally generated stimulus, a separate calibration step is required; for example, a separate step is required for each pure tone frequency. Each step requires presenting the stimulus at a specified nominal level, measuring the system output with a sound level meter or vibration meter, and adjusting a calibration control until the measured output matches the expected output. The external audio input is calibrated by presenting a stimulus from the outboard audio playback device and adjusting a calibration control in a similar fashion.

Audiometers must present stimuli over a range of levels in excess of 100 dB. Programmable attenuators are provided for controlling output level. Attenuators may be placed before or after the power amplification stage. When presenting stimuli at low levels, however, applying purely pre-amplification attenuation results in a poor signal-to-noise ratio. Therefore, audiometers must provide post-amplification attenuators. The amount of signal attenuation provided by a post-amplification attenuator depends on the transducer impedance. Therefore, audiometers are typically designed to accommodate transducers of a specified nominal impedance.

Newer hearing tests require presentation of alternative stimuli. One such newer hearing test is the Hearing In Noise Test (HINT). Originally developed to assess the benefit of hearing aids, HINT is useful for the measurement of functional hearing ability. HINT is a pre- recorded adaptive speech test that measures the Reception Threshold for Sentences (RTS) in quiet and in noise. Each of the 12 alternate forms of the test consists of a 20-sentence list. The sentences are short (5–7 syllables) and simple (first grade reading level).

As mentioned above, conventional audiometers provide only limited support for presenting alternative stimuli. In particular, when using alternative stimuli, stimulus presentation is not easily automated, stimulus level control may be inaccurate, and compensation for frequency-dependent transducer characteristics is not possible. More tests which use alternative stimuli are likely to be developed as audiological science progresses. Therefore, a useful hearing test device should provide full support for the use of arbitrary stimuli.

There are several drawbacks to the design of conventional audiometers implemented as described above:

There is no easy way to automatically control an outboard audio playback device, so presentation of externally provided stimuli cannot be automated.

Calibration is time-consuming and susceptible to operator error.

The system can only be calibrated for a specific externally provided stimulus. If a different stimulus is presented from the outboard audio playback device, the stimulus presentation level cannot be predicted.

While the calibration procedure for internally generated pure-tone stimuli effectively compensates for the frequency-dependent response of the transducer, no such compensation is possible for broad-band or externally provided stimuli.

The system is designed to be used with transducers of a specified nominal impedance. This reduces the flexibility of the system by preventing its use with transducers of different nominal impedance.

The system is designed with the assumption that the actual impedance of a transducer is equal to its nominal impedance and is constant across frequency. In practice, either of these assumptions may be false, with the result that the system may present incorrect stimulus levels.

SUMMARY OF THE INVENTION

The present invention provides a hearing test device that supports the use of arbitrary stimuli, along with a method for calibrating the device. The device is capable of performing a wider variety of hearing tests than existing audiometers, thereby improving the diagnosis and treatment of hearing disorders. The calibration method permits compensation for frequency-dependent characteristics of any transducer, thereby improving the accuracy and flexibility of the device. The calibration method is largely automated, thereby improving the speed and ease of calibration and reducing the likelihood of operator error.

The principal, but not exclusive, objects of the invention are to:

Present arbitrary acoustical or vibratory stimuli

Present stimuli over a wide range of levels, with good signal-to-noise ratios at each level Provide precise control over stimulus level Present stimuli over any transducer of reasonable quality, regardless of the impedance of the transducer Compensate for frequency-dependent modification of magnitude and phase due to the transducer and the device Automate the presentation of stimuli Automate the calibration of the system

DETAILED DESCRIPTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Figure 1:
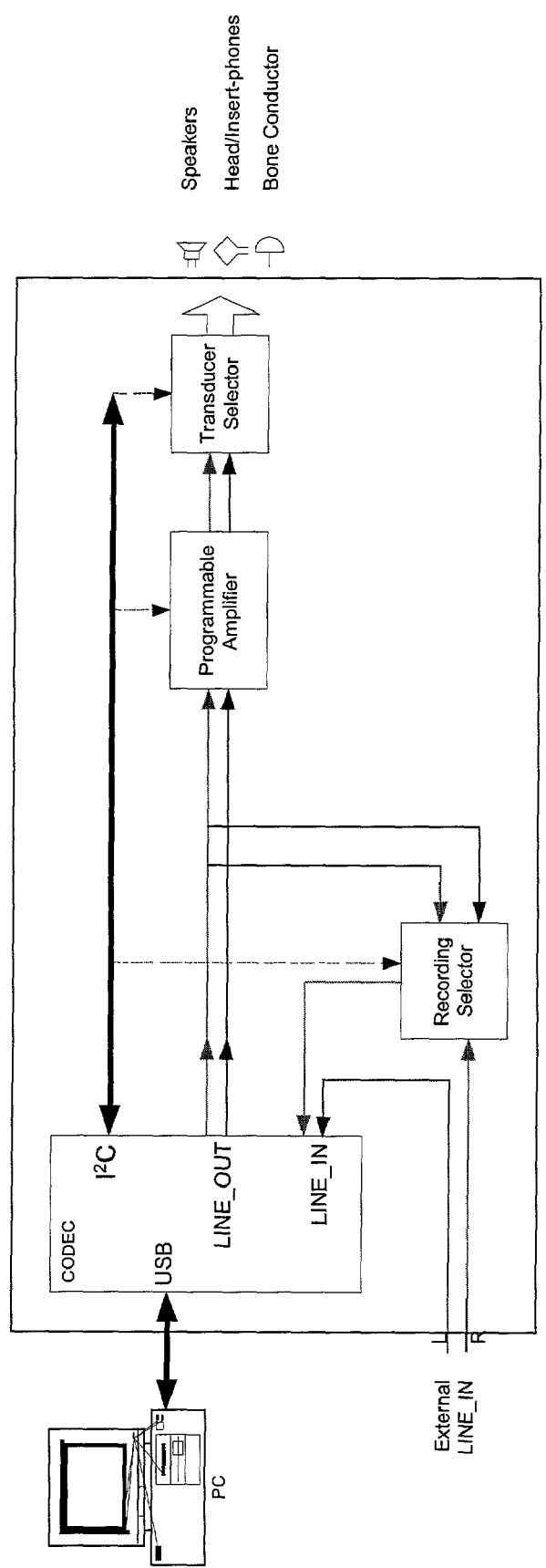
FIG. 1 is a block diagram of a hearing test apparatus in accordance with the present invention.

FIG. 1 is a block diagram of one embodiment of a hearing test device in accordance with the present invention. The principal components of the device are as follows:

- An interface for sending/receiving 2-channel digital audio signals to/from a computer.
- An interface for receiving control signals from a computer.
- Computer memory for storing digital audio signals and calibration data.
- A 2-channel digital audio codec (D/A and A/D converters).
- Programmable amplifier consisting of:
  - A fixed-gain 2-channel amplifier
  - A set of resistors located after each channel of the fixed-gain amplifier ("output attenuators"). Each resistor can be switched in or out of the signal path under computer control.
- Analog outputs for one or more acoustic and/or vibratory output transducers. Output transducers may be selected or deselected under computer control.
- Analog inputs for 2 external line-level signals. One of the two input channels must be capable of being connected to one of the two D/A converter output channels.

A computer, such as a PC, is required for operation of the device. In the illustrated embodiment, a Universal Serial Bus (USB) interface is used to provide the computer interface for control signals and for digital audio I/O, and control signals are encoded using the IIC protocol.

Figure 2:
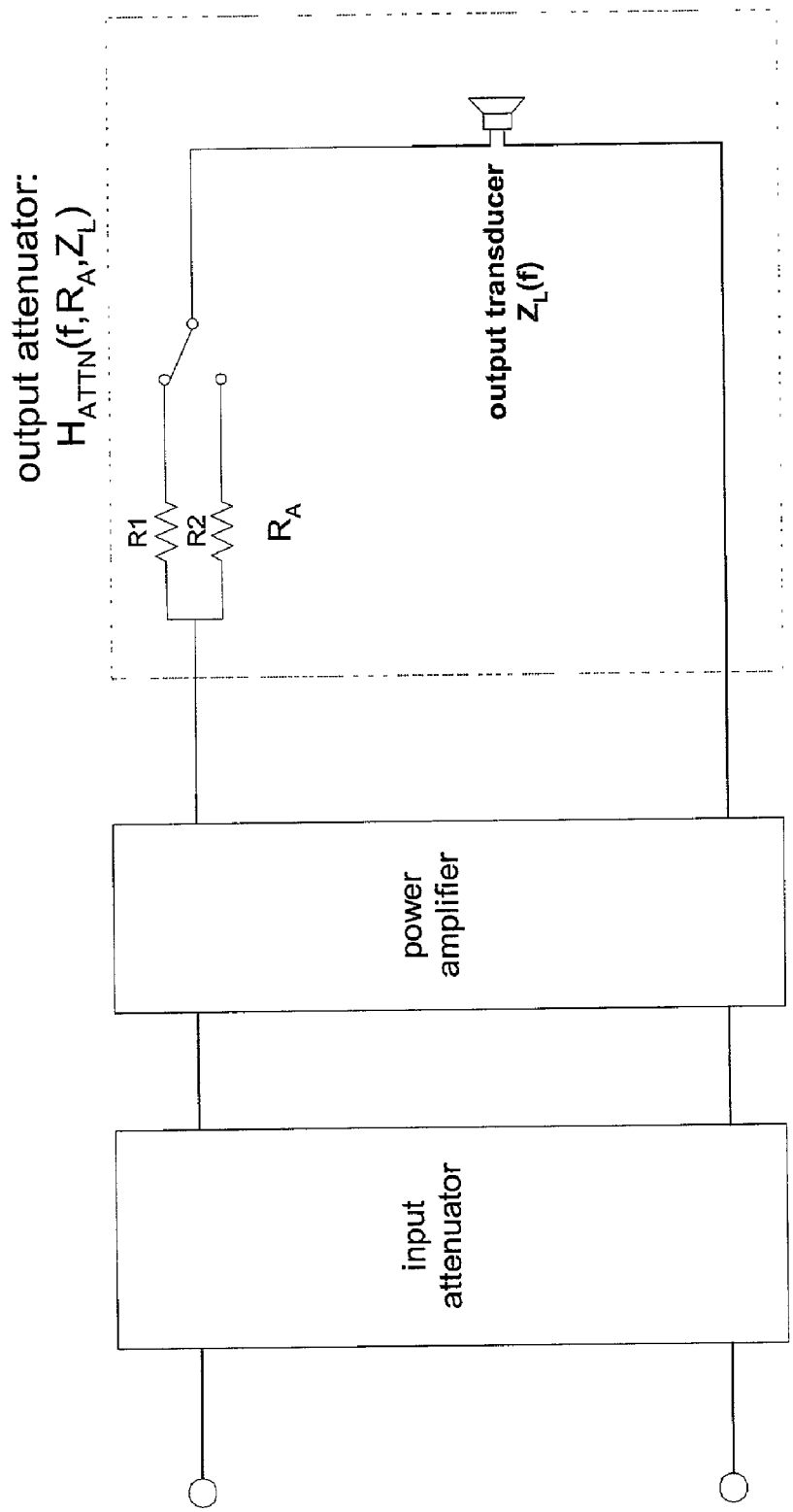
FIG. 2 is a more detailed block diagram of the programmable amplifier shown in FIG. 1.

FIG. 2 shows more detail of the programmable amplifier, which comprises digitally-controlled analog attenuators ("input attenuators") located before each channel of the fixed-gain amplifier. The programmable amplifier subsystem also includes the fixed-gain amplifier and the output attenuators.

All stimulus presentation is controlled by the computer, as follows:

1. The computer obtains a digital audio signal, either by reading a signal from memory or by generating a signal algorithmically. This allows automated presentation of arbitrary stimuli.
2. The computer applies digital filtering and attenuation to the digital audio signal. The filter and attenuation are determined by the desired stimulus presentation level together with the calibration data, as described in the next section.
3. The computer sends control signals to the device in order to configure the programmable amplifier appropriately. Appropriate settings are determined by the desired stimulus presentation level together with the calibration data, as described in the next section.
4. The computer sends the digital audio signal to the device, where it is converted to an analog signal by the codec and sent through the attenuators and fixed-gain amplifier to the output transducer(s).

The external line-level inputs and the A/D converter are required by the calibration method, as described below.

Calibration Method

Overview

Figure 3:
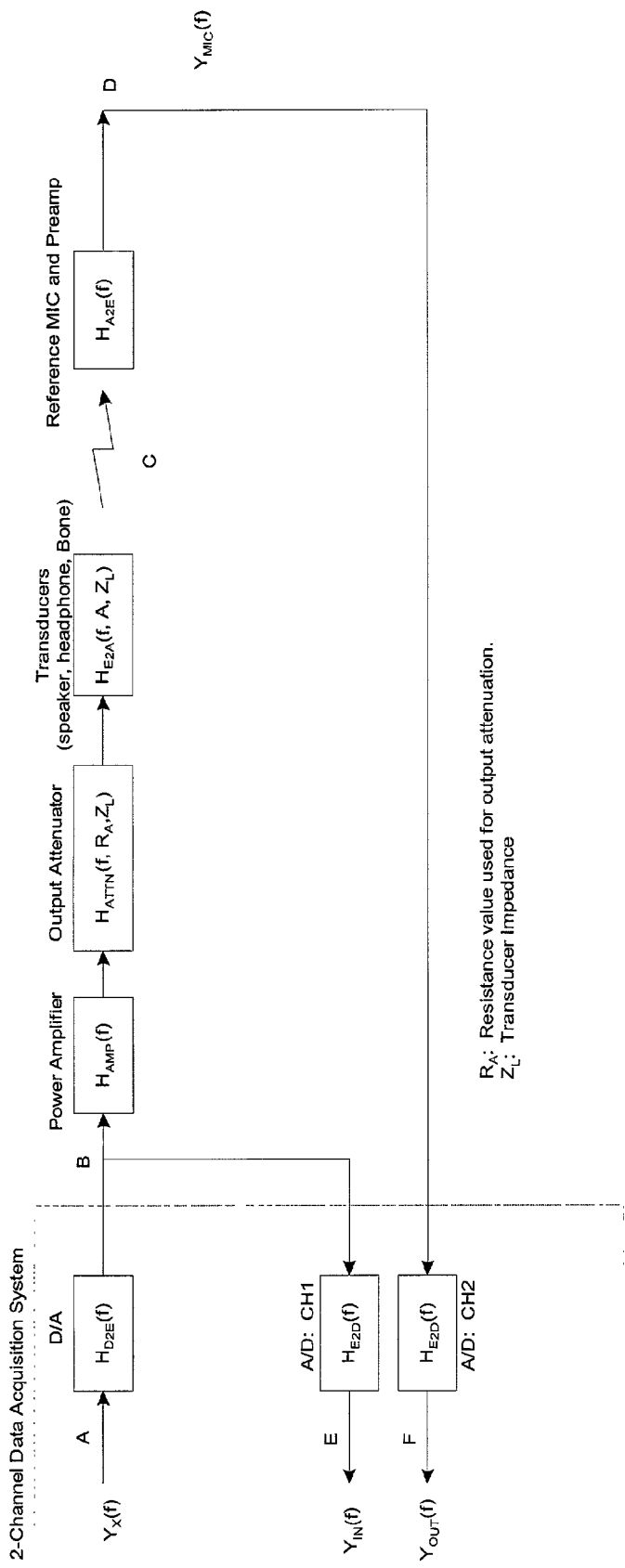
FIG. 3 is another block diagram of the apparatus shown in FIG. 1 identifying the transfer functions.

FIG. 3 shows how the device is configured for calibration. A digital signal is sent from the computer to the D/A converter (point A), where it is converted to analog (point B). From this point, the signal splits into two paths. The first path goes directly from the D/A converter output to one input channel (point E). The second path goes through the programmable amplifier and the transducer, resulting in an acoustical output (point C) which is picked up by a microphone and amplified by a microphone preamplifier (point D), after which it is routed to the other input channel (point F). The signals from the two input channels are converted to digital by the A/D converter and sent back to the computer to be recorded.

One goal of calibration is to make it possible to predict the sound pressure level (SPL) for a given digital signal. This requires knowledge of $H_{AC}(f)$, the electroacoustical transfer function of the path from point A to point C. By comparing the spectra of the two recorded signals, we can compute $H_{BD}(f)$, the transfer function of the path from point B to point D, since this is the portion of the path which differs between the two recorded signals. $H_{AB}(f)$, the transfer function of the D/A converter, is known a priori. If we know $H_{A2E}(f)$, the electroacoustical transfer function of the microphone and microphone preamplifier, then we have all the information required to derive $H_{AC}(f)$. This also allows us to design an equalization filter to flatten the transducer response.

There are two approaches to determining $H_{A2E}(f)$. If the microphone and preamplifier are provided with the device, then $H_{A2E}(f)$ can be determined in advance by performing suitable measurements. Alternatively, if the microphone and preamplifier are to be provided by the user, then an approximation of $H_{A2E}(f)$ can be derived at the time of use. This is done by assuming that the microphone and preamplifier both have flat frequency responses, and requesting the user to make a single SPL measurement to determine the microphone sensitivity.

This method allows $H_{AC}(f)$ to be determined for a particular transducer and a particular setting of the programmable amplifier. Separate measurements must be made for each transducer that will be used. As described thus far, this method also would require separate measurements to be made for every possible setting of the programmable amplifier. This would be time-consuming and impractical, especially for settings that involve a large amount of attenuation, where the acoustical signal would be too quiet to accurately record. This problem can be avoided by noting that the attenuation provided by the input attenuators and the gain provided by the fixed-gain amplifier are known a priori; the only unknown is the attenuation provided by the output attenuators, since this depends on the transducer impedance. If the transducer impedance is known, then the output attenuation can be calculated, since the values of the output attenuator resistors ($R_A$ as shown in FIG. 2) are known a priori.

In order to calculate the transducer impedance, two sets of two-channel recordings are made, using two different output attenuator settings. By combining the results of these two measurements with knowledge of the output attenuator resistor values, the transducer impedance can be derived.

The following table defines the symbols that will be used in the description of the calibration method:

| Symbol | Description | Notes |
|---|---|---|
| $H_{D2E}(f)$ | Digital-to-electrical transfer function of the D/A converter | |
| $H_{AMP}(f)$ | Electrical transfer function of power amplifier | |
| $H_{ATTN}(f, R_A, Z_L)$ | Electrical transfer function of output attenuator | $Z_L(f)$: Transducer impedance (frequency dependent) $R_A$: Output attenuator resistor value |
| $H_{E2A}(f, A, Z_L)$ | Electrical-to-acoustic transfer function of transducer | $A(f)$: Electroacoustic sensitivity of transducer, in Pascals per Watt (frequency dependent) |
| $H_{A2E}(f)$ | Acoustic-to-electrical transfer function of reference measuring microphone and preamp | |
| $H_{A-W}(f)$ | Electrical transfer function of A-weighting function | |
| $H_{E2D}(f)$ | Electrical-to-digital transfer function of A/D converters. We assume that the two channels are identical. | |
| $Y_X(f)$ | Digital spectrum of signal presented to the A/D converter at point A during normal operation | |
| $Y_{XREF}(f)$ | Digital spectrum of signal presented to the A/D converter at point A during calibration | |
| $Y_{IN}(f)$ | Digital spectrum of CH1 A/D converter output at point E | |
| $Y_{OUT}(f)$ | Digital spectrum of CH2 A/D converter output at point F | |
| $Y_{MIC}(f)$ | Spectrum of microphone/preamp output at point D | |

Calculating Transducer Characteristics

The transfer function of the output attenuator is a function of the transducer impedance $Z_L(f)$ and the output attenuator resistor value $R_A$:

$$H_{ATTN}(f, R_A, Z_L) = \frac{Z_L(f)}{Z_L(f) + R_A} \quad (1)$$

$H_{E2A}(f, A, Z_L)$ is the electroacoustic transfer function of the transducer (voltage to sound pressure). To compute it, first note that:

$$20 \log_{10} \frac{SP(f)}{p_0} = L_{sen}(f) + 10 \log_{10} \frac{[V(f)]^2}{|Z_L(f)|} \quad (2)$$

where:
SP(f): sound pressure at frequency f
$p_0$: 20 μPascal
V(f): voltage (rms magnitude) applied to the transducer
$Z_L(f)$: impedance of transducer $L_{sem}(f)$: transducer sensitivity, dB SPL per Watt Then $H_{E2A}(f, A, Z_L)$ can be computed as follows:

$$H_{E2A}(f) = \frac{SP(f)}{V(f)} = \frac{p_0 \times 10^{\frac{L_{SEN}(f)}{20}}}{\sqrt{|Z_L(f)|}} = \frac{A(f)}{\sqrt{|Z_L(f)|}} \quad (3)$$

where:

$$A(f) = p_0 \times 10^{\frac{L_{SEN}(f)}{20}} \quad (4)$$

From FIG. 3, it can be seen that the transfer function from point B to point D is:

$$H_{BD}(f,R_A,A,Z_L) = H_{AMP}(f) \times H_{ATTN}(f,R_A,Z_L) \times H_{E2A}(f,A,Z_L) \times H_{A2E}(f) \quad (5)$$

The transfer function can be calculated with $Y_{IN}(f)$ and $Y_{OUT}(f)$ measured at point E and point F:

$$H_{BD}(f, R_A, A, Z_L) = \frac{Y_{OUT}(f)}{Y_{IN}(f)} \quad (6)$$

The transfer function can be derived from the time-domain acquired signals by any of several known methods. For example, the Welch method may be used as described in P. D. Welch, "The Use of Fast Fourier Transform for the Estimation of Power Spectra", IEEE Transactions on Audio and Electroacoustics, Vol. AU-15, June 1970, pp. 70–73. It is crucial that $Y_{IN}$ and $Y_{OUT}$ be measured simultaneously in order to obtain accurate phase measurements. This is why 2-channel recording capability is required in the device.

The input signal $Y_x(f)$ used to make the measurements can be any broadband signal. The precise spectrum is not important to the calibration of the device, since frequency divides out in the transfer function calculation. However, the input signal must contain sufficient energy at all relevant frequencies.

In order to calculate $A(f)$ and $Z_L(f)$, we obtain two transfer functions, $H_{BD}(f,R_1,A,Z_L)$ and $H_{BD}(f,R_2,A,Z_L)$, measured with $R_A=R_1$ and $R_2$. We know that these transfer functions are equal to:

$$H_{BD}(f,R_1,A,Z_L) = H_{AMP}(f) \times H_{ATTN}(f,R_1,Z_L) \times H_{E2A}(f,A,Z_L) \times H_{A2E}(f) \quad H_{BD}(f,R_2,A,Z_L) = H_{AMP}(f) \times H_{ATTN}(f,R_2,Z_L) \times H_{E2A}(f,A,Z_L) \times H_{A2E}(f) \quad (7)$$

where:

$$H_{E2A}(f) = \frac{A(f)}{\sqrt{|Z_L(f)|}}$$

$$H_{ATTN}(f, R_1, Z_L) = \frac{Z_L(f)}{Z_L(f) + R_1}$$

$$H_{ATTN}(f, R_2, Z_L) = \frac{Z_L(f)}{Z_L(f) + R_2}$$

We can now solve for $Z_L(f)$ and $A(f)$:

$$Z_L(f) = \frac{H_{BD}(f, R_1, A, Z_L) \times R_1 - H_{BD}(f, R_2, A, Z_L) \times R_2}{H_{BD}(f, R_2, A, Z_L) - H_{BD}(f, R_1, A, Z_L)} \quad (8)$$

$$A(f) = \left| \frac{H_{BD}(f, R_1, A, Z_L) \times [Z_l(f) + R_1]}{H_{AMP}(f) H_{A2E}(f) \sqrt{Z_L(f)}} \right| \quad (9)$$

$R_1$, $R_2$, and $H_{AMP}(f)$ are all known a priori. Note that for calculating $Z_L(f)$, it is not necessary to know $H_{E2A}(f)$ or $H_{A2E}(f)$. It is only necessary to know $H_{BD}(f,R_1,A,Z_L)$ and $H_{BD}(f,R_2,A,Z_L)$. By contrast, knowledge of $H_{A2E}(f)$ is required in order to calculate $A(f)$ and to predict sound pressure level (see next section).

If the microphone and preamplifier are provided with the device, then $H_{A2E}(f)$ is known a priori. If the microphone and preamplifier are provided by the user, then $H_{A2E}(f)$ can be approximately derived at the time of use by the following method.

First, we assume that $H_{A2E}(f)$ is a constant, $H_{A2E}$. In order to determine $H_{A2E}$, we send a known reference signal $Y_{XREF}(f)$ to the A/D, set $R_A$ to $R_1$, and ask the user to measure the resulting sound pressure level N (in dB SPL) of the signal $Y_{MIC}(f)$. $H_{A2E}$ can then be calculated as follows:

$$H_{A2E} = \frac{\sqrt{\frac{\sum_f |Y_{MIC}(f)|^2}{M}}}{p_0 \cdot 10^{\frac{N}{20}}} \quad (10)$$

$$= \frac{\sqrt{\frac{\sum_f |Y_{XREF}(f) \cdot H_{D2E}(f) \cdot H_{BD}(f, R_1, A, Z_L)|^2}{M}}}{p_0 \cdot 10^{\frac{N}{20}}}$$

where M is the number of frequency points in the spectra. If the transducer is vibratory rather than acoustic, the user measures the force level rather than the sound pressure level.

The reference signal $Y_{XREF}(f)$ can be any signal. It does not need to be broadband.

Predicting Sound Pressure Level

During normal operation, for any given signal $Y_X(f)$ and $R_A$, the sound pressure level can be predicted as:

$$20\log_{10}\left( \sqrt{\frac{\sum_f |Y_X(f) \cdot H_{D2E}(f) \cdot H_{A'}(f)|^2}{M}} \times \frac{1}{H_{A2E}(f) \cdot p_0} \right) \quad (11)$$

where $H_A(f)$ is the transfer function from point B to point D with the chosen $R_A$ and $Z_L$, $H_{D2E}(f)$ is the frequency response of the D/A converter (which is known a priori), and M is the number of frequency points in the spectra. $H_A(f)$ can be calculated as:

$$H_{A'}(f) = H_{BD}(f, R_1, A, Z_L) \cdot \frac{H_{ATTN}(f, R_A, Z_L)}{H_{ATTN}(f, R_1, Z_L)}$$

It follows that the sound pressure level is equal to:

$$20\log_{10}\left( \sqrt{\frac{\sum_f \left| Y_X(f) \cdot H_{D2E}(f) \cdot H_{BD}(f, R_1, A, Z_L) \cdot \frac{H_{ATTN}(f, R_A, Z_L)}{H_{ATTN}(f, R_1, Z_L)} \right|^2}{M}} \times \frac{1}{H_{A2E}(f) \cdot p_0} \right) \quad (12)$$

In the special case where the microphone and preamplifier are provided by the user, $H_{A2E}(f)$ is assumed to be a constant $H_{A2E}$, which is calculated according to Equation 10. Then the sound pressure level is equal to:

$$20\log_{10}\left( 10^{N/20} \times \frac{\sqrt{\frac{\sum_f \left| Y_X(f) \cdot H_{D2E}(f) \cdot H_{BD}(f, R_1, A, Z_L) \cdot \frac{H_{ATTN}(f, R_A, Z_L)}{H_{ATTN}(f, R_1, Z_L)} \right|^2}{M}}}{\sqrt{\frac{\sum_f |Y_{XREF}(f) \cdot H_{D2E}(f) \cdot H_{BD}(f, R_1, A, Z_L)|^2}{M}}} \right) \quad (13)$$

which can be simplified to:

$$10\log_{10}\left(\frac{\sum_f \left|Y_X(f) \cdot H_{D2E}(f) \cdot H_{BD}(f, R_1, A, Z_L) \cdot \frac{H_{ATTN}(f, R_A, Z_L)}{H_{ATTN}(f, R_1, Z_L)}\right|^2}{\sum_f |Y_{XREF}(f) \cdot H_{D2E}(f) \cdot H_{BD}(f, R_1, A, Z_L)|^2}\right) + N \quad (14)$$

Note that A(f) does not appear in this equation, so it is not necessary to calculate A(f) in order to predict sound pressure. A(f) should only be calculated if it is desirable to know the transducer sensitivity for some other application.

We can also predict A-weighted sound pressure level. A-weighting is described in Allan D. Pierce, *Acoustics: An Introduction to its Physical Principles and Applications*, Acoustical Society of America, Woodbury, N.Y., 1989, p. 66.

In the case where the microphone and preamplifier are provided with the device, we modify Equation 12 as follows:

$$20\log_{10}\left(\frac{\sqrt{\sum_f \left|Y_X(f) \cdot H_{D2E}(f) \cdot H_{BD}(f, R_1, A, Z_L) \cdot \frac{H_{ATTN}(f, R_A, Z_L)}{H_{ATTN}(f, R_1, Z_L)} \cdot H_{A-w}(f)\right|^2}}{M} \times \frac{1}{H_{A2E}(f) \cdot p_0}\right) \quad (15)$$

In the case where the microphone and preamplifier are provided by the user, we modify Equation 14 as follows:

$$10\log_{10}\left(\frac{\sum_f \left|Y_X(f) \cdot H_{D2E}(f) \cdot H_{BD}(f, R_1, A, Z_L) \cdot \frac{H_{ATTN}(f, R_A, Z_L)}{H_{ATTN}(f, R_1, Z_L)} \cdot H_{A-w}(f)\right|^2}{\sum_f |Y_{XREF}(f) \cdot H_{D2E}(f) \cdot H_{BD}(f, R_1, A, Z_L)|^2}\right) + N \quad (16)$$

Equalizing the Transducer

The previous sections have described how to calculate the output attenuator transfer function $H_{ATTN}(f, R_A, Z_L)$ and the transducer transfer function $H_{E2A}(f, A, Z_L)$. Once these transfer functions are known, standard filter design techniques may be used to design an inverse filter to equalize one or both of them. Applying an equalization filter can result in improved fidelity for presentation of broadband stimuli.

Benefits of Calibration Method

The key element of the calibration method is the derivation of impedance as a complex function of frequency. This has several benefits:

The method allows the use of transducers of arbitrary impedance, thereby increasing the flexibility of the device.

The method allows the prediction of the frequency-dependent attenuation provided by the post-amplification attenuators, thereby improving the accuracy of stimulus presentation level.

The method allows the prediction of attenuation provided by large post-amplification attenuators, where it is impractical to make direct measurements due to the low level of the output signal.

The method allows the design of an equalization filter, thereby improving control over the magnitude and phase of the presented stimulus.

The method allows precise prediction and control of presentation level for arbitrary stimuli, thereby widening the scope of application of the device.

The method is largely automated, thereby improving the speed and ease of calibration and reducing the likelihood of operator error.

It will be recognized that the above-described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. In a system for presenting an audio stimulus having an input, an amplifier, an attenuator and a transducer, a method of predicting a sound pressure level emitted by the transducer comprising:

applying a broadband audio signal to the input;

inserting a first attenuation between the amplifier and the transducer;

measuring a first output from the transducer;

calculating a first transfer function for a signal path from the input to the measured first output;

inserting a second attenuation between the amplifier and the transducer;

measuring a second output from the transducer, wherein the broadband audio signal applied at the input is measured simultaneously with measuring the first and second outputs from the transducer;

calculating a second transfer function for a signal path from the input to the measured second output, wherein the first and second transfer functions are calculated as respective ratios of the first and second measured outputs to the corresponding measured inputs and wherein each of the first and second transfer functions is expressed as a product of an amplifier transfer function, an attenuator transfer function, an electrical-to-acoustical transfer function and an acoustical-to-electrical transfer function;

combining the first and second transfer functions to solve for a characteristic impedance and sensitivity of the transducer;

calculating a sound pressure level emitted by the transducer as a function of input signal and attenuation wherein the characteristic impedance $Z_L(f)$ of the transducer is calculated as:

$$Z_L(f) = \frac{H_{BD}(f, R_1 A, Z_L) \times R_1 - H_{BD}(f, R_2, A, Z_L) \times R_2}{H_{BD}(f, R_2, A, Z_L) - H_{BD}(f, R_1, A, Z_L)};$$

where: $H_{BD}(f, R_A, A, Z_L) = H_{AMP}(f) \times H_{ATTN}(f, R_A, Z_L) \times H_{E2A}(f, A, Z_L) \times H_{A2E}(f)$ $H_{AMP}(f)$ is the electrical transfer function of the amplifier $H_{ATTN}(f, R_A, Z_L)$ is the electrical transfer function of an attenuator $R_A$=output attenuator resistor value $R_1$=resistor value of first attenuation $R_2$=resistor value of second attenuation $H_{E2A}(f, A, Z_L)$ is the electrical to acoustic transfer function of the transducer $H_{A2E}(f)$ is the acoustic to electrical transfer function of a reference measuring microphone and preamp $$A(f) = p_0 \times 10^{\frac{L_{SEN}(f)}{20}}$$

$p_0$=20 µPascal $L_{sen}(f)$=transducer sensitivity.

2. The method of claim 1 wherein the sensitivity of the transducer is calculated as:

$$A(f) = \left| \frac{H_{BD}(f, R_1, A, Z_L) \times [Z_L(f) + R_1]}{H_{AMP}(f) H_{A2E}(f) \sqrt{Z_L(f)}} \right|.$$

3. The method of claim 2 wherein the sound pressure level is calculated as:

$$20 \log_{10} \left( \sqrt{\frac{\sum_f \left| Y_X(f) \cdot H_{D2E}(f) \cdot H_{BD}(f, R_1, A, Z_L) \cdot \frac{H_{ATTN}(f, R_A, Z_L)}{H_{ATTN}(f, R_1, Z_L)} \right|^2}{M}} \times \frac{1}{H_{A2E}(f) \cdot p_0} \right)$$

where: $H_{D2E}(f)$ is the frequency response of a D/A converter $Y_x(f)$=digital spectrum of signal presented to A/D converter during normal operation.

4. The method of claim 2 wherein the sound pressure level is calculated as:

$$10 \log_{10} \left( \frac{\sum_f \left| Y_X(f) \cdot H_{D2E}(f) \cdot H_{BD}(f, R_1, A, Z_L) \cdot \frac{H_{ATTN}(f, R_A, Z_L)}{H_{ATTN}(f, R_1, Z_L)} \right|}{\sum_f |Y_{XREF}(f) \cdot H_{D2E}(f) \cdot H_{BD}(f, R_1 A, Z_L)|^2} \right) + N$$

where: $Y_x(f)$=digital spectrum of signal presented to A/D converter during normal operation $Y_{XREF}(f)$=digital spectrum of signal presented to A/D converter during calibration;

N=measured sound pressure level in dB SPL $H_{D2E}(f)$ is the frequency response of a D/A converter.

5. The method of claim 2 wherein the sound pressure level is calculated as:

$$20 \log_{10} \left( \sqrt{\frac{\sum_f \left| Y_X(f) \cdot H_{D2E}(f) \cdot H_{BD}(f, R_1, A, Z_L) \cdot \frac{H_{ATTN}(f, R_A, Z_L)}{H_{ATTN}(f, R_1, Z_L)} \cdot H_{A-W}(f) \right|^2}{M}} \times \frac{1}{H_{A2E}(f) \cdot p_0} \right)$$

where: $H_{A-W}(f)$ is the electrical transfer function of A-weighting function

M=number of frequency points in spectra $H_{D2E}(f)$ is the frequency response of a D/A converter;

$Y_x(f)$=digital spectrum of signal presented to A/D converter during normal operation.

6. The method of claim 2 wherein the sound pressure level is calculated as:

$$10 \log_{10} \left( \frac{\sum_f \left| Y_x(f) \cdot H_{D2E}(f) \cdot H_{BD}(f, R_1, A, Z_L) \cdot \frac{H_{ATTN}(f, R_A, Z_L)}{H_{ATTN}(f, R_1, Z_L)} \cdot H_{A-W}(f) \right|^2}{\sum_f |Y_{XREF}(f) \cdot H_{D2E}(f) \cdot H_{BD}(f, R_1, A, Z_L)|^2} \right) + N$$

$H_{D2E}(f)$ is the frequency response of a D/A converter;

$Y_x(f)$=digital spectrum of signal presented to A/D converter during normal operation;

$H_{A-W}(f)$ is the electrical transfer function of A-weighting function;

$Y_{xREF}(f)$=digital spectrum of signal presented to A/D converter during calibration.

7. The method of claim 1 wherein the transducer is an acoustic transducer.

8. The method of claim 1 wherein the transducer is a vibratory transducer.

* * * * *